United States Patent
Brown et al.

(10) Patent No.: US 8,747,113 B2
(45) Date of Patent: Jun. 10, 2014

(54) MOLDABLE TRAY, SYSTEM, AND METHOD FOR WHITENING TEETH

(75) Inventors: Damon J. Brown, Boston, MA (US); Graham K. Philp, Jr., San Diego, CA (US); Graham K. Parish-Philp, legal representative, San Diego, CA (US)

(73) Assignee: Dentovations Inc., Boston, MA (US)

( * ) Notice: Subject to any disclaimer, the term of this patent is extended or adjusted under 35 U.S.C. 154(b) by 174 days.

(21) Appl. No.: 12/385,589

(22) Filed: Apr. 13, 2009

(65) Prior Publication Data
US 2009/0325129 A1 Dec. 31, 2009

Related U.S. Application Data

(63) Continuation of application No. PCT/US2006/040021, filed on Oct. 12, 2006.

(51) Int. Cl.
*A61C 15/00* (2006.01)
(52) U.S. Cl.
USPC .......................................................... 433/216
(58) Field of Classification Search
USPC .......... 433/34–72, 214–216, 80, 6, 24, 217.1;
425/175–177; 264/17–20;
128/859–862; 424/401, 49, 53, 435
See application file for complete search history.

(56) References Cited

U.S. PATENT DOCUMENTS

| | | |
|---|---|---|
| 3,278,520 A | 10/1966 | Klug |
| 3,278,521 A | 10/1966 | Klug |
| 3,567,823 A | 3/1971 | Yamaga et al. |
| 4,556,561 A | 12/1985 | Brown et al. |
| 4,661,070 A | 4/1987 | Frieman |
| 4,684,517 A | 8/1987 | Clipper et al. |
| 4,976,955 A | 12/1990 | Libin |
| 4,980,152 A | 12/1990 | Frazier et al. |
| 4,983,380 A | 1/1991 | Yarborough |
| 5,000,942 A | 3/1991 | Libin |
| 5,009,885 A | 4/1991 | Yarborough |

(Continued)

FOREIGN PATENT DOCUMENTS

| | | |
|---|---|---|
| EP | 0539315 | 4/1993 |
| WO | WO 9940870 A1 | 2/1999 |
| WO | WO 0126576 A1 | 4/2001 |
| WO | PCT/US2006/040021 | 10/2006 |

OTHER PUBLICATIONS

International Search Report (ISR) in parent application No. PCT/US 06/40021, filed Oct. 12, 2006, (9 pages) dated Jul. 10, 2007.

*Primary Examiner* — Yogesh Patel
(74) *Attorney, Agent, or Firm* — Shlesinger, Arkwright & Garvey LLP

(57) ABSTRACT

Tooth whitening system includes a moldable dental tray of sufficiently moldable material so that a user can form the tray to substantially match the configuration of the user's teeth, in use. Moldable dental tray includes a raised region and a valley that are adjacent to and free of contact with a corresponding raised region and valley of a user's tooth adjacent a user's gum line. Thus, a tooth provided on the moldable dental tray is free of contact with the user's gingiva, in use. Tooth whitener includes a carrier, a whitening agent, and a sufficiently adhesive so that both the tooth whitener and the moldable dental tray are adhered to a user's tooth for a sufficiently long period of time to achieve a whitening of the user's tooth by the whitening agent. Tooth whitener and tray can be made of organic, natural materials.

13 Claims, 2 Drawing Sheets

(56) References Cited

U.S. PATENT DOCUMENTS

| | | | |
|---|---|---|---|
| 5,032,178 | A | 7/1991 | Cornell |
| 5,084,268 | A | 1/1992 | Thaler |
| 5,139,768 | A | 8/1992 | Friedman |
| 5,171,564 | A | 12/1992 | Nathoo et al. |
| 5,208,010 | A | 5/1993 | Thaler |
| 5,217,710 | A | 6/1993 | William et al. |
| 5,234,342 | A | 8/1993 | Fischer |
| 5,234,343 | A * | 8/1993 | Shoher et al. ............... 433/215 |
| 5,264,205 | A | 11/1993 | Kelly |
| 5,279,816 | A | 1/1994 | Church et al. |
| 5,290,566 | A | 3/1994 | Schow et al. |
| 5,302,375 | A | 4/1994 | Viscio |
| 5,310,563 | A | 5/1994 | Curtis et al. |
| 5,372,802 | A | 12/1994 | Barrows et al. |
| 5,376,006 | A | 12/1994 | Fischer |
| 5,395,241 | A | 3/1995 | Kandelman |
| 5,403,577 | A | 4/1995 | Friedman |
| 5,403,578 | A | 4/1995 | Gordon |
| 5,409,631 | A | 4/1995 | Fischer |
| 5,425,953 | A | 6/1995 | Sintov et al. |
| 5,437,858 | A | 8/1995 | Hungerbrach et al. |
| 5,573,399 | A * | 11/1996 | McClintock, II ............... 433/80 |
| 5,614,174 | A | 3/1997 | Hsu et al. |
| 5,631,000 | A | 5/1997 | Pellico et al. |
| 5,690,912 | A | 11/1997 | Campbell et al. |
| 5,693,315 | A | 12/1997 | Bevilacqua |
| 5,698,182 | A | 12/1997 | Prencipe et al. |
| 5,708,052 | A | 1/1998 | Fischer et al. |
| 5,718,886 | A | 2/1998 | Pellico |
| 5,746,598 | A | 5/1998 | Fischer |
| 5,766,574 | A | 6/1998 | Christina-Beck et al. |
| 5,780,015 | A | 7/1998 | Fisher et al. |
| 5,785,527 | A | 7/1998 | Jensen et al. |
| 5,785,957 | A | 7/1998 | Losee et al. |
| 5,792,446 | A | 8/1998 | Ashley |
| 5,797,749 | A | 8/1998 | Bertolotti et al. |
| 5,814,304 | A | 9/1998 | Wong et al. |
| 5,820,852 | A | 10/1998 | Burgess et al. |
| 5,824,289 | A | 10/1998 | Stoltz |
| 5,846,570 | A | 12/1998 | Barrow et al. |
| 5,849,266 | A | 12/1998 | Friedman |
| 5,849,269 | A | 12/1998 | Burgess et al. |
| 5,851,512 | A | 12/1998 | Fischer |
| 5,855,870 | A | 1/1999 | Fischer |
| 5,858,332 | A | 1/1999 | Jensen et al. |
| 5,879,691 | A | 3/1999 | Sagel et al. |
| 5,891,453 | A | 4/1999 | Sagel et al. |
| 5,894,017 | A | 4/1999 | Sagel et al. |
| 5,902,568 | A | 5/1999 | Ryles et al. |
| 5,922,307 | A | 7/1999 | Montgomery |
| 5,928,628 | A | 7/1999 | Pellico |
| 5,985,249 | A | 11/1999 | Fischer |
| 6,030,222 | A | 2/2000 | Tarver |
| 6,036,493 | A | 3/2000 | Sharma |
| 6,045,811 | A * | 4/2000 | Dirksing et al. ............... 424/401 |
| 6,102,696 | A | 8/2000 | Osterwalder |
| 6,136,297 | A | 10/2000 | Sagel et al. |
| 6,183,251 | B1 | 2/2001 | Fischer |
| 6,277,458 | B1 | 8/2001 | Dirksing et al. |
| 6,312,666 | B1 | 11/2001 | Oxman et al. |
| 6,419,906 | B1 | 7/2002 | Xu et al. |
| 6,517,350 | B2 | 2/2003 | Diasti et al. |
| 6,551,579 | B2 | 4/2003 | Sagel et al. |
| 6,730,316 | B2 | 5/2004 | Chen |
| 6,896,518 | B2 * | 5/2005 | Jacobs et al. ............... 433/215 |
| 7,011,523 | B2 | 3/2006 | Allred et al. |
| 7,128,899 | B2 | 10/2006 | Chen |
| 2002/0004190 | A1* | 1/2002 | Diasti et al. ............... 433/215 |
| 2002/0047222 | A1 | 4/2002 | Philp |
| 2002/0064753 | A1 | 5/2002 | Philp |
| 2003/0003421 | A1* | 1/2003 | Bestenheider et al. ........ 433/215 |
| 2003/0232310 | A1* | 12/2003 | Matthews et al. ............. 433/215 |
| 2004/0110111 | A1* | 6/2004 | Wasylucha ............... 433/29 |
| 2005/0089821 | A1* | 4/2005 | Allred et al. ............... 433/215 |
| 2005/0192348 | A1 | 9/2005 | Bar-Or et al. |
| 2005/0255054 | A1 | 11/2005 | Philp et al. |
| 2005/0260142 | A1 | 11/2005 | Philp et al. |
| 2006/0141422 | A1 | 6/2006 | Philp et al. |
| 2006/0141423 | A1 | 6/2006 | Brown et al. |
| 2006/0171903 | A1* | 8/2006 | Yamagishi et al. ............. 424/52 |
| 2007/0009857 | A1* | 1/2007 | Philp et al. ............... 433/217.1 |
| 2009/0148815 | A1 | 6/2009 | Philp et al. |
| 2009/0325129 | A1 | 12/2009 | Brown et al. |

\* cited by examiner

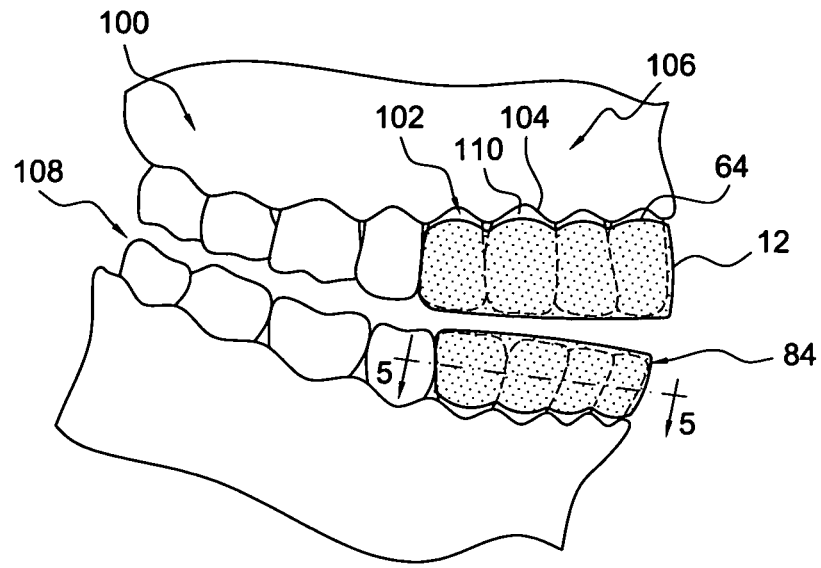
FIG. 4
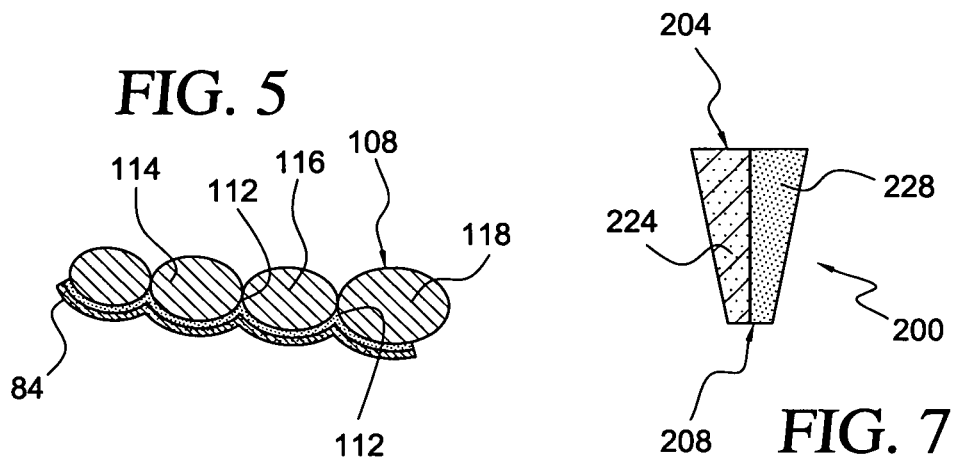
FIG. 5
FIG. 7
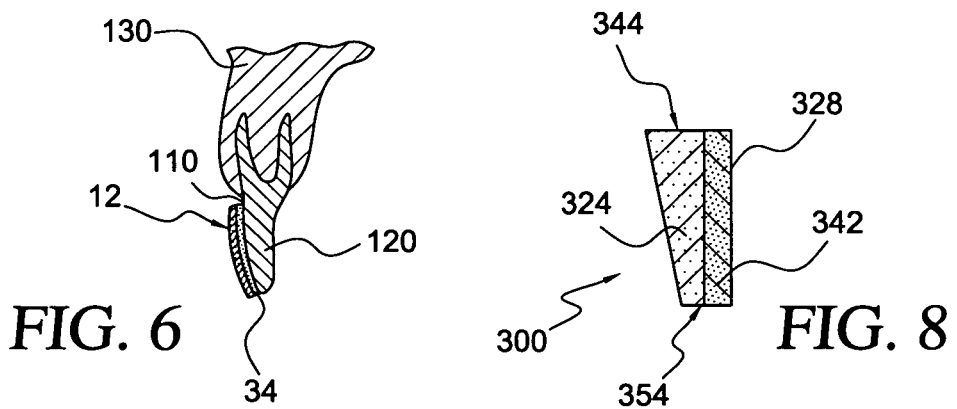
FIG. 6
FIG. 8

MOLDABLE TRAY, SYSTEM, AND METHOD FOR WHITENING TEETH

CROSS-REFERENCE TO RELATED APPLICATION

This application is a continuation of application no. PCT/US2006/040021, filed Oct. 12, 2006, and which is incorporated herein by reference.

FIELD OF THE INVENTION

The invention relates to a method of whitening teeth that will achieve effective tooth whitening results, and be usable by the consumer. In particular, the invention relates to a moldable mouth tray in the form of a moldable wax tray containing a whitening formula, and containing an oxidizing agent incorporated on top of the wax tray. Further, the invention relates to a tooth whitening device and system in which whitening formula containing a whitening agent are separate from the wax tray. Still further, the invention relates to a whitening device and compound that are comprised of natural ingredients.

BACKGROUND OF THE INVENTION

The desire for whiter, lighter teeth is considered to be desirable in today's cosmetically oriented society. The tooth structures which are affected by stains are the enamel and dentin, and the thin layer on the enamel surface, the acquired pellicle. Teeth can become discolored with age, blood, amalgam restorations, antibiotics such as tetracycline, and substances in food, beverages and tobacco and salivary fluid.

Tooth stains are generally classified as either extrinsic or intrinsic depending on whether the stain is on the surface of the tooth, within the acquired pellicle or within the tooth structure itself within the enamel or dentin. Extrinsic staining of the acquired pellicle can occur from foods or compounds, which contain toxins and other polyphenolic chemicals on the surfaces of the teeth. Intrinsic staining, on the other hand, occurs when chromogens and pre-chromogens penetrate the enamel and dentin and become tightly bound to the tooth structure. Intrinsic staining can occur when blood or amalgam products leach into the enamel and dentin. Intrinsic staining is not removed by mechanical means such as tooth cleaning and generally requires the use of chemicals, for example strong oxidizing agents such as hydrogen peroxide that can penetrate into the tooth structure to effect a change in the light absorbability of the stain chromogen and or solubility of the chromogen.

Tooth bleaching is generally accomplished by gels, pastes or liquids which contain an oxidizing agent such as hydrogen peroxide. The products from the breakdown of hydrogen peroxide, the oxygen free radicals, attach to the chromogen molecules, making them colorless and/or water soluble, allowing the tooth to appear lighter and brighter.

The most commonly used oxidizing agent is hydrogen peroxide, commonly obtained from carbamide peroxide which is mixed with an anhydrous viscous carrier containing glycerin and/or propylene glycol and/or polyethylene glycol. When in contact with water, carbamide peroxide dissociates into urea and hydrogen peroxide. The hydrogen peroxide, in the presence of water, dissociates into water and an oxygen free radical species. It is these species of highly reactive oxygen anions, which react with a stain molecule making the stain more water soluble transparent or both. This is what is responsible for teeth appearing lighter and brighter; i.e., the desired tooth whitening.

There are several consumer-based delivery systems to deliver the carbamide peroxide to the surfaces of the teeth. A common approach is to have a pre-made plastic tray. The oxidizing agent in a gel form is dispensed into the plastic tray by the consumer and the tray is worn over the teeth intermittently for a period of two weeks to several months. This approach can be cumbersome since the trays are often uncomfortable to wear and in many cases do not fit adequately causing discomfort.

Another approach is to simply paint on the oxidizing agent, carbamide peroxide, or hydrogen peroxide directly on the teeth. These products have the inherent problem of being easily removed by the lips, or tongue from the tooth surfaces which significantly reduces their effectiveness.

A common approach is to incorporate the oxidizing agent in a strip, such as shown in U.S. Pat. No. 5,891,453, and have the consumer wear the strip intermittently over a period of two weeks. These strips have the inherent problem of contacting the teeth only on the facial surfaces, as opposed to the difficult to reach interproximal surfaces, between the teeth, where most of the stain is present. Another problem with these strips is that the strips tend to slip of the tooth causing discomfort for the user.

To overcome the problems inherent in the over the counter strips, trays and paint-on products, there is a need for a relatively inexpensive and effective moldable tray which can more readily reach the interproximal areas of the teeth and be comfortable and easy for the consumer to apply and wear.

OBJECTS AND SUMMARY OF THE INVENTION

It is an object of the invention to provide a tooth-whitening, device, system, and method that overcome the drawbacks of the prior art strips, trays, and paint-on over-the-counter devices and methods.

It is a further object of the invention to provide a tooth whitening system, which provides a more accurate and more effective whitening of the teeth than previous systems.

It is a further object of the invention to provide a tooth whitening tray, system, and method, each of which is easier to use, and more accurate and more effective whitening of the teeth than previous systems.

It is yet another object of the invention to provide a tray which is easily moldable around the consumer's teeth and will cause the whitening agents to get into, and hence whiten, the interproximal areas of the teeth.

It is another object of the invention to provide a tooth whitening tray, system, and method which provide effective and accurate whitening of the teeth, while substantially precluding contact of the tooth whitener with the user's gums or gingiva, in use.

It is yet another object of the invention to provide a tray, such as a wax tray, which is easily moldable around the consumer's teeth and will cause the whitening agents to get into, and hence whiten, the interproximal areas of the teeth.

A further object of the invention is to have a wax tray which is cost-affective, enabling more people to afford to have whiter teeth.

In sum, one embodiment of the invention includes that an inventive moldable mouth tray be sufficiently moldable so that a user can accurately place and form the moldable tray around teeth to be whitened, in use.

Another embodiment of the invention includes that the inventive moldable mouth tray be made from a food grade petroleum based wax.

A further embodiment of the invention includes that the inventive moldable mouth tray be made from a natural wax. In addition, a natural tooth whitener may be used with the natural moldable mouth tray.

Tooth whitening system includes a moldable dental tray, the moldable dental tray including a moldable material, which is sufficiently moldable so that a user can form the tray to substantially match the configuration of the user's teeth, in use. Moldable dental tray includes a raised region and a valley so that, in use, the raised region and valley are adjacent to and free of contact with a corresponding raised region and valley of a user's tooth adjacent a user's gum line. Thus, a tooth provided on the moldable dental tray is free of contact with the user's gingiva, in use. The tooth whitener includes a carrier, a whitening agent, and an adhesive material, which is sufficiently adhesive so that both the tooth whitener and the moldable dental tray formed to substantially match the configuration of the user's teeth, in use, are adhered to a user's tooth for a sufficiently long period of time to achieve a whitening of the user's tooth by the whitening agent. The inventive method of use, and the moldable dental tray, are likewise described.

The inventive tooth whitener and tray can be made of organic, natural materials.

The wax will be configured thicker on the gingival side of the wax tray to enable a consumer to more easily press the wax interproximally between the teeth, enabling the whitening oxidizing agent to access these areas where most of the stains occur. This can be accomplished by manufacturing the wax tray with a slight taper, enabling the gingival edge to be thicker than the incisal edge.

Another embodiment according to the invention includes that a moldable wax tray of uniform thickness is manufactured, and another layer of wax is added on top of the uniform thickness of wax, only on the gingival side of the wax tray. The wax tray will be dimpled so that the whitening solution will more easily stay on the moldable tray.

The whitening formula gel according to the invention can be added on top of the wax tray prior to packaging as is conventionally done, or the consumer may add the whitening gel inside the moldable tray, as has been customarily done with a hard plastic dentist tray based system. In this embodiment the moldable wax tray may be a single use disposable tray, and the whitening gel may be dispensed by use of a syringe or dispensing device.

Another embodiment of the invention includes that the wax tray is overlaid with cloth fibers which may be impregnated with the whitening agent, thus eliminating the messiness of a pre-coated wax tray. Such cloth fibers are an absorbent material as will be readily apparent to a person having ordinary skill in the art. As will be appreciated, such overlaid cloth fibers may be termed an absorbent layer.

A further embodiment of the invention includes that the consumer may paint the whitening agent onto the facial surfaces of the teeth, and then immediately apply the wax tray to act as a barrier to prevent the whitening agent from being removed by the lips and tongue.

In either embodiment the wax tray or the gel may contain a tackifying agent which enables the wax tray to remain adhered to the teeth. Further, having the wax tray thicker on the gingival side enables the wax tray to be pressed interproximally to enhance mechanical retention of the wax tray, thus keeping the wax tray in place while being worn.

It is another object of the invention to use only natural ingredients in the wax and whitening gel.

As used herein, the term moldable tray means that the tray is sufficiently bendable by a user in a manner such that the moldable tray does not return to its initial original shape as it was before the moldable tray was bent by the user. That is, the moldable tray is sufficiently plastically deformable so that users can shape the moldable mouth tray to conform to the configuration and curvature of their teeth, and so that the moldable mouth tray retains that shape during the tooth whitening process. It is understood that there exist relatively hard, rigid plastic mouth trays which can be bent, yet which return to their initial unbent original condition and shape under normal use. It is likewise understood that such prior art plastic mouth trays which are bendable can be bent, contrary to their intended use, and indeed folded completely in half, for example, contrary to their intended use, so that they are permanently deformed, and are unsuited for their intended normal use in the tooth whitening process. That type of non-standard, indeed destructive, permanent plastic deformation that is contrary to the intended use of a mouth tray is, of course, not intended to be covered by the term moldable mouth tray as used herein.

Relative terms such as up, down, upper, lower, left, and right are for convenience only and are not intended to be limiting. Throughout the specification it will be appreciated that the term "substantially" is to be understood to mean "generally."

BRIEF DESCRIPTION OF THE DRAWINGS

FIG. 4 is a side view of the wax trays of FIGS. 1 and 2, in use;

FIG. 5 is a top sectional view of the wax tray of FIG. 4, in use;

FIG. 6 is a side sectional view of the wax tray of FIG. 4, in use;

FIG. 7 is a sectional view similar to FIG. 3 of a wax tray according to another embodiment of the invention of the invention; and FIG. 8 is a sectional view similar to FIG. 7 of a wax tray according to further embodiment of the invention of the invention.

DETAILED DESCRIPTION OF THE INVENTION

Figure 1:
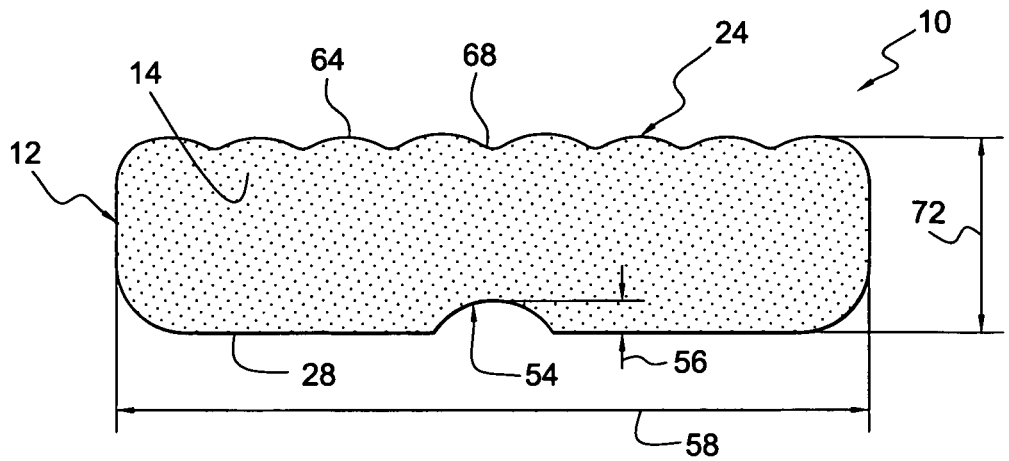
FIG. 1 is at front view of the wax tray according to the invention with whitening agent on one side only, suited for use on upper teeth.
Figure 2:
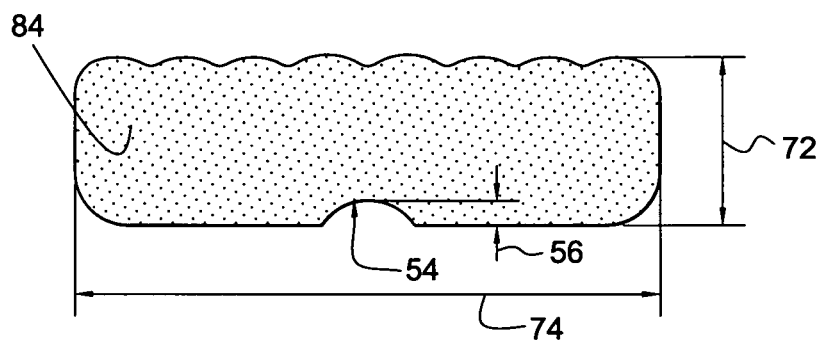
FIG. 2 is a front view of the wax tray according to the invention with whitening agent on one side only, suited for use on lower teeth.

FIGS. 1-6 show a first embodiment of a tooth whitening device 10 according to the invention.

Whitening device 10 may have an inner face 14 configured for facing a person's teeth, in use, and an outer face 18 on an opposite side of device 10, which outer face 18 will face away from the user's mouth in use.

Tooth whitening device 10 may include an upper mold 12 or whitening device, which may be made of a wax and configured in the form of a dental tray. Upper tray 12 may include an upper gingival region 24 and a lower, incisal portion 28. As shown, upper gingival region may include one or more raised regions 64 and one or more valleys 68. As will be readily appreciated, raised regions 64 and valleys 68 may be configured to conform substantially to the configuration of a user's teeth adjacent the gum line of a user, as may be appreciated from considering FIG. 4, which will be described in more detail below.

Lower incisal portion 28 may be substantially flat, as shown, given that for most users, no shaping to conform to the substantially flat plane of the incisal portion of a user's teeth is required.

A reduced portion 54 may be provided on tooth whitening device 10, as shown in FIG. 1. Reduced portion 54 may be provided between the left and right sides of wax tray 10, such as substantially in the middle of wax tray 10, as shown in FIG. 1. Reduced portion 54 has been found to enhance the use of wax tray 10, thanks to the reduction in wax material in that region so that, in use, it is even easier for a user to conform wax tray 10 to the user's teeth during the whitening process.

Reduced portion 54 may be of various heights, depending on the intended use, the moldability of the wax used for wax tray 10, and the like. A height 56 of reduced portion 54 may be 5 mm in a case where a height 72 of wax tray 10 has a height of 20 mm. Given the height dimension of upper mold 12, a width 74 of upper mold 12 may be 72 mm, for example. These dimensions may be used for upper wax tray 12.

In the case of a lower mold or wax tray 84, a height 56 of reduced portion 54 may be 3 mm, and the overall height 72 of lower mold 84 may be 18 mm in that case. Further, given those height dimensions of lower mold 84, a width 74 of lower mold may be 56 mm.

Figure 3:
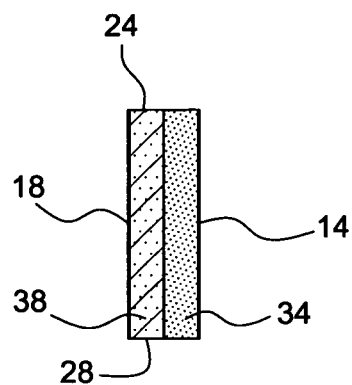
FIG. 3 is a sectional view of the wax tray of FIGS. 1 and 2.

FIG. 3 shows a sectional view of teeth whitening device 10, which may be a side sectional view of either or both of upper mold 12 and lower mold 84.

The cross section may be substantially rectangular, as shown. A first material, such as a food grade wax may be provided adjacent outer face 18 in a region 38. This may be considered a wax base 38. An impregnated front region 34 may be provided adjacent face 14, and be impregnated with a tooth whitener. Tooth whitener formulation according to the invention will be described in detail below. The front region 34 will be material which retains a tooth whitener for a sufficiently long period of time that it whitens a user's teeth to the desired degree of whiteness in the desired time period. In the case where the whitening compound is applied by the manufacturer, the whitener will have a desired shelf-life, so that the effectiveness of the tooth whitener will not have diminished by the time the user applies it to his or her teeth.

Impregnated front region 34 may likewise be a layer of whitening agent which the user has applied himself, such as by applying a whitening gel 34 to wax base 38 prior to the user placing the wax base on his teeth to be whitened. In both embodiments, that is, the case in which the manufacturer has applied the whitener prior to packaging, and the case in which the user has applied the whitener himself, the whitener may be a gel, as well as a gel which contains a tackifying agent which enhances the adhesion of the wax tray and the whitening agent to the teeth, in use.

FIG. 4 shows the use of both upper mold 12 and lower mold 84 during the whitening process. As shown, both upper wax tray 12 and lower wax tray 84 need only cover the typical eight forwardmost teeth 102 in a user's mouth 100. The rear teeth, such as the rear teeth of lower teeth 108, are generally not seen under normal circumstances by the user, nor by others. Thus, there is generally no need to whiten rearmost ones of teeth 108. To reduce the possibility that the whitener in the moldable tray 12 contacts a portion 104 of the user's gums 106, moldable tray 12 is configured so that raised regions 64 and valleys 68 may be configured to conform substantially to the configuration of a user's teeth adjacent a gum line 104 of a user's upper teeth of forwardmost teeth 102, yet with a sufficient space 110 between gum line 104 and raised region 64, for example, so that no or substantially no whitener contacts the a user's gum adjacent gum line 104, as shown.

FIG. 5 is a top sectional view of lower wax tray 84 on lower teeth 108, taken along line 5-5 of FIG. 4. It should be noted that thanks to the inventive valleys 68 and raised regions 64, as well as to the use of wax tray 84, the whitening compound in or on impregnated front region 34 has reached interstitial regions 112 between respective adjacent one's of adjacent lower teeth 114 and 116, as well as the interstitial region 112 between adjacent teeth 116 and 118 as shown.

FIG. 6 is a side sectional view of upper wax tray 12 in place on upper teeth 120. It should be noted that, thanks to the inventive configuration of raised regions 64 and valleys 68 configured to be adjacent, but not cover gum 130 of the user's mouth, the whitening agent, which may cause irritation to the user's gum 130, does not substantially contact gum 130, thanks to gap 110 between tray 12 and gum 130. Impregnated front region or whitening gel 34 is adjacent outer faces of upper front teeth 120, as likewise described above.

FIG. 7 illustrates another embodiment of a whitening device 200 according to the invention that has a tapered or wedge-shaped cross section. This wedge-shape cross section, which has additional wax adjacent a top gingival portion 204 of outer face and outer face 224 enhances the user's ability to form wax tray 200, in use, so as to further ensure that the whitening agent is pressed into the interstitial regions of the user's teeth, which interstitial regions are regions which typically require more whitening than other regions of the user's teeth.

The wedge-shaped cross section may be narrower at a lower incisal portion 208.

It is likewise contemplated that the whitening agent may be evenly distributed from top gingival portion 204 to lower incisal portion 208, depending on the intended use.

FIG. 8 illustrates another preferred embodiment of a whitening device 300, such as the illustrated wax tray, according to the invention. Wax tray 300 may include an outer face 324 and an inner face 328.

As shown, wax tray 300 may have a tapered or wedge-shaped cross sectional configuration, along the lines described in connection with FIG. 7. That is, the wedge-shaped configuration may be substantially trapezoidal, may have additional wax and additional whitening agent at an upper portion 344 or the amount of whitening agent and the thickness of the region adjacent inner face 328 may be substantially the same from upper region 344 to a lower region 354.

Whitening agent may be applied adjacent inner face 328, or, as shown, a material capable of retaining and being impregnated with the whitening agent may be provided, such as a porous material and, indeed a cloth-like material 342.

The following formulations may be used as a whitening agent in accordance with the invention.

Carbopol® 940 is a trademark of Noveon, Inc. for water-soluble and water-swellable synthetic polymeric materials to be used as thickening, suspending, or emulsifying agents. Carbopol® 940 is a typical carbomer; i.e., a synthetic polymer of acrylic acid. Carbomers are used as emulsion stabilizers or thickening agents in cosmetic products.

It is contemplated that each of these formulations may be used with any of the above-described embodiments.

Formulation

| Ingredient | % by Weight |
|---|---|
| Glycerin | 73.982% |
| Urea Hydrogen (Carbamide) Peroxide | 15.0% |
| Methyl Hydrogenated Rosinate | 10.0% |
| Carbopol ® 940 | 0.478% |
| Triethanolamine | 0.322% |
| Spearmint Oil | 0.156% |
| Sodium Saccharin | 0.062% |

Formulation Range

| Ingredient | % by Weight |
|---|---|
| Glycerin | 10%-95% |
| Urea Hydrogen (Carbamide) Peroxide | .001-40% |
| Methyl Hydrogenated Rosinate | .001-35.0% |
| Carbopol ® 940 | .001-10% |
| Triethanolamine | .001-5% |
| Spearmint Oil | 0.00-2% |
| Sodium Saccharin | 0.00-2% |

Natural Formulation

| Ingredient | % by Weight |
|---|---|
| Water | 10.85% |
| Hydrogen Peroxide | 5% |
| Glycerin- Kosher Vegetable | 81.14 |
| Xanthan Gum | 1% |
| Certified Organic *Aloe Vera* (*Aloe Barbadensis*) | 0.01% |
| Natural Flavors | 2% |

Natural Formulation-Range

| Ingredient | % by Weight |
|---|---|
| Water | 0.000-50% |
| Hydrogen Peroxide | 0.001-40% |
| Glycerin- Kosher Vegetable | 5-90% |
| Xanthan Gum | 0.001% |
| Certified Organic *Aloe Vera* (*Aloe Barbadensis*) | 0.001-5% |
| Natural Flavors | 0.001-2% |

Types of Natural Wax

| |
|---|
| Beeswax |
| Carnauba wax |
| Jojoba wax |
| Euphorbia certified wax |

It is contemplated that one or both of the spearmint oil and the sodium saccharin may be omitted from each of these formulations, and likewise used with any of the above-described embodiments.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention or limits of the claims appended hereto.

The invention claimed is:

1. A tooth whitening system, comprising:
   a) a generally flat moldable wax dental tray;
   b) the generally flat moldable wax dental tray being sufficiently moldable so that a user can form the moldable wax dental tray to generally match the configuration of the user's teeth, in use;
   c) the moldable wax dental tray including an upper gingival region and a lower incisal portion, the lower incisal portion being generally flat, and the upper gingival region being generally parallel to the lower incisal portion; and the dental tray including a left side and a right side, the left side being generally parallel to the right side; and the dental tray including a reduced portion provided generally centrally on the lower incisal portion; and the upper gingival region including a raised region and a valley, and configured so that, in use, the raised region and valley are adjacent to and free of contact with a corresponding raised region and valley of a user's tooth adjacent a user's gum line, respectively, and so that, in use, a gap is defined between the respective raised regions and valleys;
   d) the moldable wax dental tray including an absorbent layer provided on a region which faces a user's teeth;
   e) a tooth whitener provided on the absorbent layer of the moldable wax dental tray, the tooth whitener including:
      i) a carrier;
      ii) a whitening agent; and
      iii) an adhesive material, the adhesive material being sufficiently adhesive so that both the tooth whitener and the moldable wax dental tray formed to substantially match the configuration of the user's teeth, in use, are adhered to a user's tooth for a sufficiently long period of time to achieve a whitening of the user's tooth by the whitening agent;
   e) the tooth whitener includes, as a percent by weight:

| | |
|---|---|
| i) glycerin | 10%-95%; |
| ii) urea hydrogen peroxide | .001-40%; |
| iii) methyl hydrogenated rosinate | .001-35.0%; |
| iv) carbomer | .001-10%; |
| v) triethanolamine | .001-5%; |
| vi) spearmint oil | 0.00-2%; and |
| vii) sodium saccharin | 0.00-2%; and | g) the raised region and valley of the moldable wax dental tray, in use, with the tooth whitener on the moldable wax dental tray, causing the tooth whitener to be free of contact with the corresponding raised region and valley of the user's tooth and gum adjacent the gum line, so as to substantially prevent contact of the tooth whitener with the user's gum, in use.

2. Tooth whitening system as in claim 1, wherein:
   a) the tooth whitener includes material applied by the user and provided on a region on the moldable wax dental tray that faces the user's teeth, in use.

3. Tooth whitening system as in claim 1, wherein:
   a) the moldable wax dental tray includes a natural wax.

4. Tooth whitening system as in claim 1, wherein:
   a) the moldable wax dental tray includes a beeswax.

5. Tooth whitening system as in claim 1, wherein:
   a) the moldable wax dental tray includes a jojoba wax.

6. Tooth whitening system as in claim 1, wherein:
a) the absorbent layer includes cloth fibers.

7. A method of whitening teeth, comprising:
a) providing a generally flat moldable wax dental tray;
b) the generally flat moldable wax dental tray being sufficiently moldable so that a user can form the moldable wax dental tray to generally match the configuration of the user's teeth, in use;
c) the moldable wax dental tray, including an upper gingival region and a lower incisal portion, the lower incisal portion being generally flat, and the upper gingival region being generally parallel to the lower incisal portion; and the dental tray including a left side and a right side, the left side being generally parallel to the right side; and the dental tray including a reduced portion provided generally centrally on the lower incisal portion; and the upper gingival region including a raised region and a valley, and configured so that, in use, the raised region and valley are adjacent to and free of contact with a corresponding raised region and valley of a user's tooth adjacent a user's gum line, respectively, and so that, in use, a gap is defined between the respective raised regions and valleys;
d) the moldable wax dental tray including an absorbent layer provided on a region which faces a user's teeth;
e) providing a tooth whitener on the absorbent layer of the moldable wax dental tray, the tooth whitener including:
  i) a carrier;
  ii) a whitening agent; and
  iii) an adhesive material, the adhesive material being sufficiently adhesive so that both the tooth whitener and the moldable dental tray formed to substantially match the configuration of the user's teeth, in use, are adhered to a user's tooth for a sufficiently long period of time to achieve a whitening of the user's tooth by the whitening agent;
f) the tooth whitener includes, as a percent by weight:

| | |
|---|---|
| i) glycerin | 10%-95%; |
| ii) urea hydrogen peroxide | .001-40%; |
| iii) methyl hydrogenated rosinate | .001-35.0%; |
| iv) carbomer | .001-10%; |
| v) triethanolamine | .001-5%; |
| vi) spearmint oil | 0.00-2%; and |
| vii) sodium saccharin | 0.00-2%; and | g) the raised region and valley of the moldable wax dental tray, in use, with the tooth whitener on the moldable wax dental tray, causing the tooth whitener to be free of contact with the corresponding raised region and valley of the user's tooth and gum adjacent the gum line, so as to substantially prevent contact of the tooth whitener with the user's gum, in use;
h) placing the moldable wax dental tray with tooth whitener thereon on the user's teeth;
i) molding the moldable wax dental tray to conform to the configuration of the user's teeth; and
j) leaving the tooth whitener and molded wax dental tray on the user's teeth a sufficiently long time so as to whiten the user's teeth.

8. Method of whitening teeth as in claim 7, wherein:
a) the tooth whitener includes an impregnated region provided on a region of the moldable wax dental tray that faces the user's teeth, in use.

9. Method of whitening teeth as in claim 7, wherein:
a) the tooth whitener includes material applied by the user and provided on a region on the moldable wax dental tray that faces the user's teeth, in use.

10. Method of whitening teeth as in claim 7, wherein:
a) the moldable wax dental tray includes a natural wax.

11. Method of whitening teeth as in claim 7, wherein:
a) the absorbent layer includes cloth fibers.

12. A tooth whitening system, comprising:
a) a generally flat moldable wax dental tray;
b) the generally flat moldable wax dental tray being sufficiently moldable so that a user can form the moldable wax dental tray to generally match the configuration of the user's teeth, in use;
c) the moldable wax dental tray including an upper gingival region and a lower incisal portion, the lower incisal portion being generally flat, and the upper gingival region being generally parallel to the lower incisal portion; and the dental tray including a left side and a right side, the left side being generally parallel to the right side; and the dental tray including a reduced portion provided generally centrally on the lower incisal portion; and the upper gingival region including a raised region and a valley, and configured so that, in use, the raised region and valley are adjacent to and free of contact with a corresponding raised region and valley of a user's tooth adjacent a user's gum line, respectively, and so that, in use, a gap is defined between the respective raised regions and valleys;
d) the moldable wax dental tray including an absorbent layer provided on a region which faces a user's teeth;
e) a tooth whitener provided on the absorbent layer of the moldable wax dental tray, the tooth whitener including:
  iv) a carrier;
  v) a whitening agent; and
  vi) an adhesive material, the adhesive material being sufficiently adhesive so that both the tooth whitener and the moldable wax dental tray formed to substantially match the configuration of the user's teeth, in use, are adhered to a user's tooth for a sufficiently long period of time to achieve a whitening of the user's tooth by the whitening agent;
f) the tooth whitener includes, as a percent by weight:

| | |
|---|---|
| glycerin | 73.982%; |
| urea hydrogen peroxide | 15.0%; |
| methyl hydrogenated rosinate | 10.0%; |
| carbomer | 0.478%; |
| triethanolamine | 0.322%; |
| spearmint oil | 0.156%; and |
| vii), sodium saccharin | 0.062%; and | g) the raised region and valley of the moldable wax dental tray, in use, with the tooth whitener on the moldable wax dental tray, causing the tooth whitener to be free of contact with the corresponding raised region and valley of the user's tooth and gum adjacent the gum line, so as to substantially prevent contact of the tooth whitener with the user's gum, in use.

13. Tooth whitening system as in claim 12, wherein:
a) the absorbent layer includes cloth fibers.

* * * * *